United States Patent [19]

Robert et al.

[11] Patent Number: 4,665,053
[45] Date of Patent: May 12, 1987

[54] PEPTIDE DERIVATIVES, THE PREPARATION AND THEIR USE AS ELASTASE INHIBITORS

[75] Inventors: Ladislas Robert, Santeny; William Hornebeck, Saint Cyr l'Ecole; Elemer Moczar, Gif-sur-Yvette, all of France

[73] Assignee: Centre National de la Recherche Scientifique, Paris, France

[21] Appl. No.: 610,111

[22] Filed: May 14, 1984

[30] Foreign Application Priority Data

May 16, 1983 [FR] France .................................. 83 08052

[51] Int. Cl.$^4$ ........................ A61K 37/02; C07K 5/08; C07K 5/10
[52] U.S. Cl. ..................................... 514/18; 514/844; 530/330; 530/331
[58] Field of Search ................. 424/177; 260/112.5 R; 514/12, 18, 844; 530/330, 331

[56] References Cited

U.S. PATENT DOCUMENTS 4,362,716 12/1982 Bouchaudon et al. .............. 424/177
4,439,425 3/1984 Tarcaay et al. ...................... 424/177

OTHER PUBLICATIONS

Hornebeck et al., *Biological Pharmacology*, 34, No. 18, 3315–3321 (1985).

*Primary Examiner*—Delbert R. Phillips
*Attorney, Agent, or Firm*—Cushman, Darby & Cushman

[57] ABSTRACT

Lipopeptides of the formula, $R-X-(P_1)_x-(L-Ala-L-Ala-P_2)-A$ wherein x is 0 or 1, R is the acyl residue of a hydrophobic carboxylic acid, $P_2$ is, for instance, L—Ala, L—Val, L—Pro—L—Ala or L—Pro—L—Val, $P_1$ is a residue of an amino acid or an oligopeptide formed from 2–8 amino acids, X represent a divalent group or a direct covalent bond and A represents the C-terminal portion (modified or not) of $-(P_1)_x-(Ala-Ala-P_2)$. These lipopeptides can be used as elastase inhibitors.

12 Claims, No Drawings

PEPTIDE DERIVATIVES, THE PREPARATION AND THEIR USE AS ELASTASE INHIBITORS

The present invention relates to new bifunctional synthetic lipopeptides which can be considered both as inhibitors of elastolytic activity and protectors of elastic fibers. These substances are in effect capable of recognizing elastic fiber and becoming fixed onto it and also are capable of recognizing and neutralizing the active site of elastases.

The elastase inhibitors of the present invention exhibit, principally, the following advantages: they have no antigenic character; they are biodegradable; they also have the property of reaching the site of their action and being fixed thereat.

It is known that elastin is an elastic fibrous protein of the conjunctive tissue of the vertebrae and is present in vascular walls, skin, lungs, cartiliges, ligaments and other tissue. While elastin is the most resistant protein of the organism, its degradation increases particularly rapidly in certain pathologic states and in general during the course of ageing, in all tissue rich in elastin such as vascular walls and derma; see L. Robert, in "Precis de physiologie cutanee", under the direction of J. Meynadier, Ed. de la Porte Verte (1980) p. 155-173.

Only few proteases can attack elastin. These proteases are called elastases or proteases of the elastase type. Such enzymes are pancreatic elastase and cellular elastases: leucocytic and platelet elastases, and elastases of macrophages, fibroblasts and smooth arterial muscular cells.

These enzymes are capable of degrading elastin in the tissue and organs mentioned above, and of contributing to the development of illnesses such as arteriosclerosis, emphysema, arthrosis, diabetes, and also to aging of the connective tissue of the organism.

The activity of elastases is controlled and regulated by natural inhibitors which are present, on the one hand, in blood plasma, as $\alpha$-1-antitrypsin and $\alpha$-2-macroglobulin and, on the other hand, in the tissular secretions such as bronchial secretions; see for example Hornbeck et al, "Control of elastic tissue destruction by elastase inhibitors" in DEYL, ADAM Eds, Connective Tissue Research: Chemistry, Biology and Physiology, p. 233-216, A. R. Liss. Inc., New York, 1981.

Moreover, numerous bacteria, capable of penetrating into the organism, secret elastolytic proteases whose action contributes in a substantial manner to their pathogenic effect.

It is also known that the progression of malignant tumors (cancers, sarcoma) in the organism and the formation of metastases, often fatal to a person who is ill, are also conditioned by the secretion of elastase type proteases; see for example, Biological significance of Elastase-like enzymes in Arteriosclerosis and Human breast cancer. W. Hornebeck, D. Brechemier, G. Bellon, J. J. Adnet and L. Robert in: P. Straulli, A. J. Barrett, A. Baici eds. Proteinases and tumor invasion, vol. 6, of ORTC Monograph series (1980) pp. 117-141, (Raven Press, New York). Such enzymes are capable of destroying the surrounding tissue, thus rendering possible the penetration of malignant cells in blood circulation and causing the invasion of the organism by the tumor.

For all these reasons, it is important to be able to provide inhibitors capable of controlling the activity of elastases.

However, certain ones of these elastases have a useful activity, even indispensible, for the organism, for example in the digestion of phagocyte bacteria by macrophages.

It appears then important to provide both elastase inhibitors and protectors of elastic fibers. It also appears preferable to be able to provide elastase inhibitors which are capable of acting selectively at the level of the elastic fibers whose integrity is indispensible for the good functioning of the organism.

In effect, enzymatic hydrolysis of elastin by elastases can be considered as a determining factor in numerous pathologies of elastic tissue: arteriosclerosis, emphysema and certain skin diseases. In the living organism this proteolysis results from a disequilibrium between the amount of proteases having an elastolytic activity, on the one hand, and on the other hand, the amount of natural inhibitors of plasmitic or tissular orgin. One of the therapeutic approaches which has been envisaged in the case of a deficiency, of genetic or functional origin, of these protease inhibitors, consists in using inhibitors of natural substitution ($\alpha$-1-antitrypsin).

However, the use of natural inhibitors presents numerous disadvantages, among which are the cost of treatment and risk of accidents of immunologic orgin. On the other hand, the elastase inhibitors used in experimental animal therapy, in the case of emphysema, have the disadvantage of possessing strong toxicity.

The present invention relates to new lipopeptides of the formula:

$$R-X-(P_1)_x-(L-Ala-L-Ala-P_2)-A \qquad (I)$$

wherein x represents 0 or 1;

R represents the acyl residue of a hydropholic carboxylic acid, such as (i) an aliphatic carboxylic acid having 6-25 carbon atoms and which can include, optionally, 1-5 double bonds, (ii) an alicyclic carboxylic acid having 6-25 carbon atoms, (iii) an aryl carboxylic acid or (iv) an arylaliphatic carboxylic acid, the aryl group of which comprises 1-2 rings and the aliphatic group of (iv) having 1-18 carbon atoms. The aromatic groups of said aryl or aryl aliphatic groups can optionally be substituted;

$P_2$ represents the residue of an amino acid or dipeptide, linked by its N-terminal end to the adjacent L—Ala group and can be selected from the group consisting of the following amino acids and dipeptides: —L—Ala—, —L—Val—, —Gly—, —L—Met—, —L—Pro—, —L—Leu—, —L—Pro—L—Val—, —L—Pro—L—Ala—, —L—Pro—L—Phe—, —L—Pro—L—Leu—, —L—Pro—L—Met— and —L—Pro—Gly—;

$P_1$ represents the residue of an amino acid or oligopeptide formed from 2-8 L-amino acids, the said amino acids being selected from the group consisting of glycine, alanine, valine, methionine, leucine, isoleucine, proline, phenylalanine, serine, cysteine, cystine, arginine, tyrosine, ornithine, lysine and glutamic acid, wherein $P_1$ is linked to RX— by its N-terminal group and $P_2$ is linked to A by its C-terminal group, Ala is the conventional representation for alanine, X represents a direct covalent bond linking R either to the N-terminal group (—NH—) or the first amino acid of $P_1$ (case where x=1) or to the N-terminal group (—NH—) of the first Ala group represented to the left in Formula I (case where x=0), or X is a divalent group having 2-10 carbon atoms and functions as an "arm" between the R group and the remainder of the molecule of the compound defined by Formula I, and A represents the C-terminal portion of the peptide —$(P_1)_x$—(Ala—Ala—$P_2$)—A, A being selected from a —$CO_2H$ carboxylic group or a derivative thereof, —CHO, —$CONH_2$, —$COCH_2Cl$ and —$CH_2OH$.

Representative derivatives of Formula I include, principally, those for which R represents the acyl residue of a fatty acid having 6-20 carbon atoms such as lauric acid or oleic acid or the residue of another organic acid having hydrophobic properties such as the residue of chenodeoxycholic acid, of cholic acid and the like; or indeed R— represents, for example, the acyl residue of a phenylalkanoic acid, optionally substituted on the benzene ring (for example by halogen, trifluoromethyl, hydroxyl or lower alkyl having 1-3 carbon atoms groups); when X is a divalent group functioning as an "arm", it is for example, a —Z—$(CH_2)_n$—CO— group, Z representing —O— or —NH—, and n being a whole number ranging from 5 to 20; the "arm" X can be substituted by one or more groups such as —OH, —$NH_2$— and —COOH, in a manner to contribute to the solubilization of the compound or to permit the optional derivatization of the compound I. Preferably the oligopeptide that represents —$(P_1)_x$—(-L—Ala—L—Ala—$P_2$)— does not possess more than 10 amino acids; it being understood that the C-terminal group that represents A can be not only a carboxylic group or a derivative thereof but also one of the groups indicated above.

Representative derivatives of the carboxylic group that can represent A, include principally, esters and in particular esters of the formula —CO—OY, Y being an aliphatic group or an aryl or arylaliphatic group, optionally substituted.

Y is in particular an alkyl group having 1-5 carbon atoms or a phenyl or alkylphenyl group, optionally substituted.

Representative other derivatives of the carboxylic group that can represent A, include metallic salts, principally alkali or alkaline earth metal salts (in particular, sodium, potassium, calcium, etc.) salts, ammonium salts and salts formed with amino products such as, for example, ethanolamine, lysine, arginine, betaines, pyridoxine (considered as cofactor of the lysyl-oxydase intervening in the synthesis of elastin) and other basic molecules, including vitamins.

The invention also relates to a process for preparing the compounds of Formula I, in accordance with known procedures for the preparation of peptides and derivatives thereof.

The invention particularly relates to a process for preparing compounds of formula I, wherein there is utilized as an initial reactant, a compound of Formula II,

H—$X_1$—$(P_1)_x$—(L—Ala—L—Ala—$P_3$)—$A_1$ (II)

wherein $X_1$ has the same meaning as X or indeed represents a direct covalent bond between H— and —$P_1$—;

$P_3$ has the same meaning as $P_2$, or $P_3$ represents a —L—Pro— group, or indeed $P_3$ represents a direct covalent bond between $A_1$ and the immediately adjacent —L—Ala—group;

$A_1$ represents a —$CO_2H$, —CO—OY (Y being defined above), —CHO or —$CONH_2$ group; and x is defined as above.

The process of the present invention comprises reacting the said initial reactant, optionally present in the form of an addition salt such as the hydrochloride, with a reactant of Formula III,

R—$X_2$—$Z_1$ (III)

wherein

R is defined above;

$X_2$ has the same meaning as X when $X_1$ represents a covalent bond, and $X_2$ represents a direct coaalent bond between R and $Z_1$ when $X_1$ has the same meaning as X; and $Z_1$ is a reactive group permitting the reaction of R—$X_2$—$Z_1$ with the compound of Formula II so as to eliminate or remove a compound, $Z_1H$, and to form a compound of Formula IV,

R—X—$(P_1)_x$—(L—Ala—L—Ala—$P_3)_y$—$A_1$ (IV);

In the situation where $P_3$ represents the —L—Pro-group, the compound of Formula IV is reacted with an amino acid of the L series selected from valine, alanine, phenylalanine, leucine, methionine and glycine, or with a derivative of one of said amino acids, (in particular a derivative whose C-terminal group is an A group such as defined above) so as to obtain a derivative of Formula I. If desired the resulting compound can be transformed into any other compound of Formula I in accordance with known procedures, in particular by replacing the terminal A or $A_1$ groups with any other terminal group set forth in the definition of A given above.

In a preferred embodiment, the process of the present invention exhibits the following characteristics taken singly or in combination:

(a) $Z_1$ is, for example, a halogen such as a chloride or bromide;

(b) in preparing a compound of Formula I in which A represents —$CH_2OH$, compound IV (with P=L—Pro) is reacted with a derivative of an amino acid for which the C-terminal group is —$CH_2OH$—; the said derivative (such as valinol) is reacted in the presence of N-methyl morpholine and t-butyl carbonyl chloride; see principally G. W. Anderson et al, J. Am. Chem. Soc., 89, 4012, 1967;

(c) in preparing a compound of Formula I for which A represents —CHO, compound of Formula I for which A represents —$CH_2OH$ is submitted to the action of an oxidation agent such as, for example, dimethylsulfoxide (Pfitzner et al, J. Am. Chem. Soc., 87, 7661, 1965), in the presence of an appropriate catalyst such as phosphoric acid or dichloro acetic acid (C. R. Thompson, Biochemistry, 12, 47, 1973);

(d) in preparing a compound of Formula I in which A represents —$COCH_2Cl$, the compound IV ($P_3$=L—Pro) is reacted with a derivative of an amino acid whose C-terminal group is —CO—$CH_2Cl$ (see for example C. R. Thompson et al, Biochemistry, 12, 44, 1973);

(e) in preparing a compound of Formula I for which A represents the ester group —CO—OY, the compound of Formula I (A=$CO_2H$) is reacted with a selected alcohol in the presence of a dehydrating agent, such as thionyl chloride; and (f) in preparing a compound of Formula I for which A represents —$CONH_2$, the compound of Formula IV ($P_3$=L—Pro) is reacted with an amino acid whose C-terminal group is —CONH$_2$, by the mixed anhydride method (Thompson et al, Biochemistry, 12, 57, 1973).

The compounds of Formula I exhibit interesting properties. They possess, principally, the dual properties of inhibiting the activity of elastase type proteases and they fix on elastic fiber.

Moreover, they do not have appreciable toxicity in active doses. However, the compounds of Formula I for which A represents —CO—CH$_2$Cl have a certain toxicity, generally at doses greater than 20 mg/kg. However, these compounds have a very high elastase inhibiting activity, so that their therapeutic index is not less favorable than other compounds of Formula I.

The present invention also relates to the use of the compounds of Formula I as an elastase inhibitor and/or as a protector of elastic fiber, principally in compositions comprising a compound of Formula I with a suitable excipient.

The compounds of Formula I are useful, for example, as medicines as the principal treatment or complementary treatment in the case of arteriosclerosis, pulmonary emphysema, arthrosis, diabetes and certain tumors in which the elastases can be implicated.

The compositions of the invention are principally pharmaceutical compositions comprising, as an active component, at least one compound of Formula I, optionally in admixture with an appropriate excipient.

These pharmaceutical compositions are administered parenterally, rectally, topically or orally, or by the inhalation of aerosols.

To this effect the compositions of the present invention can be provided in the form of aqueous solutions (injectable or drinkable solutions), solutions packaged under pressure as aerosols, emulsions, semi-solid preparations (creams, suppositories), or in the form of a lyophilized powder to be diluted or contained in an ingestible capsule or gelatin.

In the pharmaceutical composition of the present invention, with the exception of lyophilized powders, the compounds of Formula I are present generally in an amount of 0.1 to 5 weight percent.

The posology depends principally as a function of the manner of administration and the therapeutic effect sought. For example in adults it can vary from 50 mg to 5 g of active component per day.

The compounds of Formula I also exhibit interesting properties when they are applied to the skin, principally, inhibiting properties of cutaneous elastolysis. In particular the compounds of Formula I conserve or restore the suppleness of the skin and prevent or retard the formation of wrinkles, principally on the skin of the face, neck and hands (antiaging effect). The present invention thus relates to the use of the compounds of Formula I for this purpose.

The compounds of Formula I are then capable of improving the appearance of the skin and the present invention also relates to a cosmetic compositions for the skin comprising at least one compound of Formula I.

These cosmetic compositions can also include at least one adjuvant or excipient conventionally employed in cosmetic compositions for the skin. Moreover, these compositions for the skin can be provided, for example, in the form of a cream, gel, emulsion or an aqueous, alcoholic or hydroalcoholic solution.

The concentration of the compound of Formula I in these compositions for the skin ranges generally from 0.1 to 2 weight percent.

The adjuvants generally present in these cosmetic compositions are, for example, perfumes, dyes, preservatives, thickening agents and emulsifiers.

These compositions for the skin constitute principally creams, milks or lotions for the body, hands or face, including sunscreen creams, milks or lotions.

The present invention also relates to cosmetic treatment process comprising applying to the skin at least one compound of Formula I using a cosmetic composition such as defined above.

The following non-limiting examples illustrate the invention.

EXAMPLE 1

Preparation of Oleoyl-L-Alanyl-L-Alanyl-L-Prolyl-L-Alanine 3.65 g (0.01M) of L-Alanyl-L-Alanyl-L-Proyl-Alanine (hydrochloride) prepared by a known method are dissolved in a mixture of 60 ml of 90% ethanol and 3.35 g of triethylamine. To the resulting solution there is slowly added, with stirring, at 4° C., 1 g (0.025M) of oleoyl chloride over a 15 minute period. The resulting mixture is stirred again for 4 hours at ambient temperature.

The ethanol is then removed under vacuum, and to the residue there are added 100 ml of water. The pH is then adjusted to 8.5 by the addition of triethylamine and the excess oleic acid is extracted by petroleum ether. Thereafter the pH of the aqueous phase is adjusted to 4 by the addition of acetic acid. The resulting oleoyl peptide is extracted with ethyl acetate.

The solvent is removed under a vacuum and the residue is dissolved in a minimum of ethyl acetate. Crystallization is primed by the addition of petroleum ether. The desired product has the following characteristics: Melting point=115°–120° C.; and $\alpha_D = -76°$ (C=0.5%, ethanol).

EXAMPLE 2

Preparation of lauroyl trialanine 1 g of tri-alanine is dissolved in 15 ml of 80% ethanol in the presence of 0.6 g (0.83 ml) of triethylamine. To the resulting solution there are slowly added, with stirring, and at ambient temperature, 1.1 g (1.19 ml) of lauroyl chloride.

The mixture is then left to stand for 2 hours at ambient temperature at which point 5 ml of water, are added and the mixture is then extracted with petroleum ether. 30 ml of water are added to the lower phase which is then left to stand for 1 hour at ambient temperature. The crystals which form are then filtered off, and washed with petroleum ether and water.

On recrystallization in 80% alcohol the desired product has the following characteristics: Melting point=219° C.; $\alpha_D = -86°$ (C=0.5%, ethanol).

EXAMPLE 3

Oleoyl-L-Alanyl-L-Alanyl-L-Prolyl-L-Aninal (3a) Methyl ester of Oleoyl-L-Alanyl-L-Alanyl-L-Proline 3.5 g of oleic acid are dissolved in 1.2 ml of tetrahydrofuran. To this solution there are added at −15° C., 1.32 ml of N-methyl morpholine and 1.50 ml of t-butyl-carbonyl chloride.

The mixture is stirred 10 minutes at this temperature, after which there are added 3.08 g of the hydrochloride of the methyl ester of L-Alanyl-L-Alanyl-L-Proline, dissolved in a mixture of 10 ml of dimethylformamide and 1.2 ml of N-methyl morpholine.

The temperature of the resulting mixture is permitted to rise to 0°, at which point the mixture is stirred for 1 hour at this temperature. Thereafter the mixture is left to stand overnight at ambient temperature.

The crystals which precipitate on addition of N-methyl morpholine hydrochloride are filtered off. The solvent of the mother liquor is expelled under vacuum and the desired substance is crystallized in an ethyl acetate-hexane mixture. $\alpha_D = -76°$ (C=0.5% ethanol). Rf: 0.5, silica bed, methanolchloroform 5:95 v/v.

(3b) Oleoyl-L-Alanyl-L-Alanyl-L-Proline 1.07 g of the methyl ester of Oleoyl-L-Alanyl-L-Alanyl-L-Proline are dissolved in 10 ml of methanol. To this solution are added 3 ml of an aqueous solution of NaOH (1M) and the mixture is left to stand for 3 hours at ambient temperature at which point the pH is adjusted to 4 using HCl. The solvent is removed under vacuum.

The residue is then taken up in ethylacetate and the desired product is crystallized in ether-ethylacetate. $\alpha_D = -78°$(C=0.5% ethanol).

(3c) Oleoyl-Alanyl-Alanyl-Prolyl-Alaninol 1.04 g (2 mM) of Oleyl-Alanyl-Alanyl-Proline is dissolved in 20 ml of dimethyl formamide.

There are then added, at $-15°$ C., 0.24 ml (2.2 mM) of N-methyl morpholine and 0.29 ml (2.2 mM) of t-butyl carbonyl chloride. The mixture is stirred for 10 minutes at this temperature at which point 0.156 ml of L-alaninol is added. The temperature of the resulting mixture is permitted to rise to 0° C. and the mixture is then stirred for 2 hours at this temperature. The mixture is then left to stand overnight at ambient temperature. The solvent is then removed under vacuum and the residue is taken up in ethyl acetate and this phase is washed successively with water, with a 5% aqueous solution of HCl and with a 5% aqueous solution of sodium carbonate.

The solvent is then removed under vacuum and the residue is dissolved in a minimum of ethyl acetate. Crystallization is primed by the addition of petroleum ether yielding deliquescent crystals, having the following characteristic: $\alpha_D = -72°$(C=0.5, ethanol).

(3d) Oleoyl-Alanyl-Alanyl-Prolyl-Alaninal 2.9 g (5 mM) of Oleoyl-Alanyl-Alanyl-Prolyl-Alaninol are dissolved in 18 ml of chloroform. To this solution are added 2 ml of dimethylsuifoxide and 3.1 g (15 mM) of dicyclohexylcarbodiimide.

There is then added to the stirred solution 0.86 ml (15 mM) of 90% phosphoric acid in one hour, distributed in 6 equal doses.

After 4 hours of stirring, the solvent is removed under vacuum and the residue is taken up in 30 ml of chloroform. The solution is cooled to $-30°$ C., and the resulting crystals (dicyclohexyl urea) are separately filtered off. The mother liquor is washed with water. The desired substance can be isolated starting with the aqueous phase by thin layer preparative chromatography. $\alpha_D = -70°$(C=0.5%, ethanol). $R_f$=0.8, silica bed, chloroform-methanol = 15:1.

EXAMPLE 4

Preparation of Oleoyl-trialanine 2 g of L-Alanyl-L-Alanyl-L-Alanine are dissolved in 30 ml of 80% ethanol in the presence of 1.5 g of triethylamine.

To this solution are slowly added, with stirring, 4.0 g (4.4 ml) of oleoyl chloride.

The mixture is then stirred for 2 hours at ambient temperature at which point there are added 50 ml of water, followed with 1 ml of acetic acid.

The resulting precipitate is filtered off and washed with petroleum ether and water.

The desired substance is crystallized in alcohol and exhibits the following characteristics: Melting point=200° C.; $\alpha_D = -60°$(C=0.5%, ethanol).

EXAMPLE 5

Preparation of Caproyl-L-Alanyl-L-Alanyl-Alanine 1.5 g of L-Alanyl-L-Alanyl-L-Alanine are dissolved in 20 ml of 75% ethanol containing 1.56 ml of triethylamine.

To this solution there are slowly added with stirring at ambient temperature, 1.35 ml of caproyl chloride in 15 minutes.

The mixture is then left to stand for 2 hours at ambient temperature at which point 30 ml of water and 2 ml of acetic acid are added thereto.

The mixture is then again left to stand for 2 hours at 0° C. at which point the crystals formed are filtered off and washed twice with 5 ml of ice water and ether.

The desired substance is recrystallized in 70% alcohol and the desired product exhibits the following characteristics: Melting point=226° C., $\alpha_D = -43°$ (C=0.5%, ethanol).

EXAMPLE 6

Preparation Of Oleoyl-L-Alanyl-L-Alanyl-L-Prolyl-L-Valine 0.98 g of L-Alanyl-L-Alanyl-L-Prolyl-L-Valine (hydrochloride) is dissolved in 15 ml of absolute ethanol containing 1 ml of triethylamine.

To this solution there are slowly added, with stirring, at 4° C., 1.26 ml of oleoylchloride, over a 15 minute period. The mixture is again stirred for 4 hours at ambient temperature.

At this point the pH is adjusted to 8.5 by the addition of NaOH, and the solvent is expelled under vacuum. The residue is then triturated with petroleum ether and the petroleum ether decanted.

The residue is then taken up in 30 ml of water; the pH is adjusted to 4 by the addition of acetic acid; and the oleoyl peptide is extracted with ethyl acetate. The solvent is then expelled under vacuum, and the product crystallizes in an ethylacetate-petroleum ether mixture. The desired product exhibits the following characteristics: Melting point=70° C. (deliquescent); $\alpha_D = -72°$ (C=0.5%, ethanol).

In a similar manner the following derivatives of Formula I have been prepared

| | Melting Point °C. | $\alpha_D$* |
|---|---|---|
| Lauroyl-L-Alanyl-L-Alanyl-L-Alanine | 219 | −86 |
| Oleoyl-L-Alanyl-L-Alanyl-L-Alanine | 200 (decompo- | −60 |

-continued

| | Melting Point °C. | $\alpha_D$* |
|---|---|---|
| | (sition) | |
| Stearoyl-L-Alanyl-L-Alanyl-L-Alanine | 212 | −80 |
| Oleoyl-L-Alanyl-L-Alanyl L-Prolyl-L-Valinol | | −70 |
| Oleoyl-L-Alanyl-L-Alanyl-L-Prolyl-L-Valinal | | −68 |

*C = 0.5%, ethanol

Study of the properties of the compounds of Formula I

1. In vitro tests (1a) Interaction of these compounds with soluble elastin

Soluble elastin has been purified starting with a large ligament of adult ox by a method using 0.1N NaOH at the boil. Preparation of insoluble and soluble elastins, L. Robert and W. Hornebeck, in "The Methodology of Connective Tissue Research", Ed. D. A. Hall (Joynson-Bruvvers Ltd., Oxford,) pp. 81–104, 1976. In order to study the adsorption of the oleoyl derivatives on these polymers, the oleoyl-(Ala)$_2$-Pro-Ala and oleoyl-(Ala)$_2$-Pro-Val derivatives have been synthesized using radiolabelled oleic acid.

-(Ala)$_2$-Pro Ala specific activity: $2.3 \times 10^3$ cpm/nanomole.

-(Ala)$_2$-Pro Val specific activity: $2.2 \times 10^3$ cpm/nanomole.

Note: "Ol" is an abbreviation for: oleoyl.

The elastin (at different concentrations) and these radio active compounds (at different concentrations) are incubated for 24 hours at 37° C. in 1 ml of a buffer solution (100 mM Tris HCl, CaCl$_2$ 5 mM, NaN$_3$ 0.02%, pH=8.0).

The tubes are centrifuged at 10,000 g and the residue hydrolyzed by 1M KOH in the presence of 80% ethanol. The radioactivity contained in these hydrolysates is quantified and the results expressed in mmole of substance absorbed per mg of elastin.

The results obtained show that these compounds are fixed onto the elastin.

(1b) These substances and principally the alaninal derivatives act as elastase inhibitors.

Purified elastases employed: hog pancreatic elastase (120 U/mg) and purified human leucocytic elastase starting from the spleen.

Molar concentration of these enzymes: pancreatic elastase: $4 \times 10^{-9}$M; leucocytic elastase: $10 \times 10^{-9}$M.

The enzymatic activity of these elastases is followed by hydrolysis of specific synthetic substrates: N-succinoyltrialanine paranitroanilide, acetyl-bis alanylprolyl-alanine paranitroanilide at a final concentration of 1.25 mM in a Tris/HCl buffer, pH=8–8.6. The variation in optical density at 410 nm is followed directly in a Beckman type Acta C III spectrophotometer.

In the inhibition tests, the oleoyl compounds are preincubated 15 minutes with the elastases before determing the residual enzymatic activities.

The results are reported in Table I.

TABLE I

| Compound studied (inhibitor) | Enzyme | Molar ratio inhibitor/enzyme | Percent inhibition |
|---|---|---|---|
| Ol(Ala)$_2$ Pro Alanine | Pancreatic elastase | $4 \times 10^4$ | 15% |
| Ol(Ala)$_2$ Pro Alaninal | Pancreatic elastase | $4 \times 10^4$ | 85% |
| Ol(Ala)$_2$ Pro Alanine | Leucocytic elastase | $4 \times 10^4$ | 5% |
| Ol(Ala)$_2$ Pro Valine | Leucocytic elastase | $4 \times 10^4$ | 51% |
| Ol(Ala)$_2$ Pro Alaninal | Leucocytic elastase | $4 \times 10^4$ | 90% |

(1c) Elastin pretreated with these substances is partially resistant to enzymatic hydrolysis by the elastases.

For these tests, elastin has been radiolabelled with tritium borohydride NaBH$_4$, specific activity: $1.7 \times 10^5$ cmp/mg.

1 mg of elastin is treated with 10 ml of a solution of different compounds in 1 ml of Tris HCl buffer, pH-8.0, for 24 hours; the mixture is centrifuged and the insoluble elastin washed with 1 ml of buffer. 0.05 mg of pancreatic elastase is then added and hydrolysis of the polymer is quantified by measurement of the radioactive peptides liberated during the course of the hydrolysis.

The results obtained are set forth in Table II.

TABLE II

| Compound studied | Molar ratio Inhibitor/enzyme | Percent inhibition relative to samples without pretreatment |
|---|---|---|
| H(Ala)$_2$ Pro Valine | $5 \times 10^4$ | 0 |
| H(Ala)$_2$ Pro Alanine | $5 \times 10^4$ | 0 |
| Ol(Ala)$_2$ Pro Valine | $5 \times 10^4$ | 46% |
| Ol(Ala)$_2$ Pro Alaninal | $5 \times 10^4$ | 98% |

2. In vivo study of the inhibiting action of Oleoyl-bis-alanyl-proline-alanine towards the enzymatic degradation of cutaneous elastic fibers induced by intradermal injection of pancreatic elastase For these tests, young Garenne rabbits (1 month) have been employed. 3 types of intradermal injections (volume: 0.25 ml; solvent: phosphate buffer, pH 7.0) have been performed on the backs of the test animals.

1. Control injection: injection of 0.25 ml of phosphate buffer only;

2. Injection of hog pancreatic elastase: 10 micrograms (1.2 units $4 \times 10^{10}$ mole) in 0.25 ml of buffer; and 3. Injections of 50–250 micrograms of Ol—(Ala)$_2$—Pro—Ala ($8 \times 10^{-8}$ to $3 \times 10^{-7}$ mole) in 0.25 ml of buffer followed by an injection at the same site of 10 micrograms (1.2 units, $4 \times 10^{-10}$ mole) of pancreatic elastase in 0.25 ml of buffer.

Different samples of rabbit skin are then treated in histology in order to permit visualization of elastic fibers.

The histologic observation and studies of quantitative morphometry reveal:

that 40–60% of elastic isssue are preserved in the case of pretreatment with the oleoyl derivative (molar ratio of inhibitor/enzyme=$2 \times 10^2$); and that 60–80% of elastic tissue are preserved in the case of pretreatment of the tissue with the Oleoyl derivative (molar ratio, inhibitor/enzyme=$10^3$).

Conclusions (a) The substances studied: Ol—(Ala)$_2$—Pro—Ala, Ol—(Ala)$_2$—Pro—Val and Ol—(Ala)$_2$—Pro—Ala—CHO act as elastase inhibitors and (b) These compounds are linked to the elastin, and in the form absorbed onto the elastic fibers, are capable of considerably reducing the elastolytic action of elastases, and that in vivo as well as in vitro.

What is claimed is:

1. Lipopeptide of the formula

R—X—(L—Ala—L—Ala—P₂)—A     (I)

wherein
R represents the acyl residue of a hydrophobic carboxylic acid selected from
(i) an aliphatic carboxylic acid having 6-25 carbon atoms,
(ii) an alicyclic carboxylic acid having 6-25 carbon atoms,
(iii) an aryl carboxylic acid wherein the aryl moiety has 1-2 rings, and
(iv) an aryl aliphatic carboxylic acid wherein the aliphatic moiety has 1-8 carbon atoms,
P₂ represents the residue of an amino acid or dipeptide linked by its N-terminal end to the adjacent L—Ala group and selected from the group consisting of —L—Ala—, —L—Val—, —Gly—, —L—Met—, —L—Leu—, —L—Pro—L—Val—, —L—Pro—L—Ala—, —L—Pro—L—Phe—, —L—Pro—L—Leu—, —L—Pro—L—Met— and —L—Pro—Gly—;
Ala a represents alanine;
X represents a direct covalent bond between R and the N-terminal group,—NH—, of the adjacent Ala moiety or X is a divalent group having 2-10 carbon atoms so as to constitute an arm between the R group and the remainder of the molecule of the compound of Formula I; and
A represents the C terminal portion of the peptide-(Ala-Ala-P₂)-A and is selected from the group consisting of—CO₂H or a derivative thereof,—CHO,—CONH₂,—COCH₂Cl and—CH₂OH.

2. The lipopeptide of claim 1 wherein R represents the acyl residue of a fatty acid having 6-20 carbon atoms, the residue of chenodeoxycholic acid, the residue of cholic acid, or acyl residue of a phenylalkanoic acid.

3. The lipopeptide of claim 2 wherein said fatty acid is lauric acid or oleic acid.

4. The lipopeptide of claim 1 wherein X is —Z—(CH₂)ₙ—CO— wherein Z represents —O— or —NH—, and n represents a whole number ranging from 5 to 20.

5. Lipopeptide of the formula

R—X—(L—Ala—L—Ala—P₂)—A     (I)

wherein
R represents the acyl residue of a fatty acid having 6-20 carbon atoms,
P₂ represents the residue of an amino acid or dipeptide linked by its N-terminal end to the adjacent L—Ala group and selected from the group consisting of —L—Ala—, —L—Val—, —Gly—, —L—Met—, —L—Leu—, —L—Pro—L—Val—, —L—Pro—L—Ala—, —L—Pro—L—Phe—, —L—Pro—L—Leu—, —L—Pro—L—Met— and —L—Pro—Gly—;
wherein P₂ is linked to A by its C-terminal group;
Ala represents alanine;
X is a divalent group having 2-10 carbon atoms so as to constitue an arm between the R group and the remainder of the molecule of the compound of Formula I; and
A is selected from the group consisting of —CO₂H or a derivative thereof, —CHO, —CONH₂, —COCH₂Cl and —CH₂OH.

6. The lipopeptide of claim 1 wherein A represents —CO—OY wherein Y is an aliphatic, aryl or arylaliphatic group.

7. The lipopeptide of claim 1 selected from the group consisting of
(1) oleoyl-L-alanyl-L-alanyl-L-prolyl-alanine,
(2) lauroyl trialanine,
(3) oleoyl-alanyl-alanyl-proline,
(4) oleoyl-alanyl-alanyl-prolyl-alaninol,
(5) oleoyl-alanyl-alanyl-prolyl-alaninal,
(6) caproyl-L-alanyl-L-alanyl-L-alanine,
(7) lauroyl-L-alanyl-L-alanyl-L-alanine,
(8) oleoyl-L-alanyl-L-alanyl-L-alanine,
(9) stearoyl-L-alanyl-L-alanyl-L-alanine,
(10) oleoyl-L-alanyl-L-alanyl-L-proline,
(11) oleoyl-L-alanyl-L-alanyl-L-prolyl-L-alanine,
(12) oleoyl-L-alanyl L-alanyl-L-prolyl-L-valine,
(13) oleoyl-L-alanyl-L-alanyl-L-prolyl-L-alaninol,
(14) oleoyl-L-alanyl-L-alanyl-L-prolyl-L-valinol,
(15) oleoyl-L-alanyl-L-alanyl-L-prolyl-L-alaninal, and
(16) oleoyl-L-alanyl-L-alanyl-L-prolyl-L-valinal.

8. A method for inhibiting elastases or protecting elastic fibers comprising employing as the elastase inhibitor or as the elastic fiber protector, the lipopeptide of claim 1.

9. The method of claim 8 wherein said lipopeptide is employed as an inhibitor of elastase of the skin or as a protector of the skin.

10. A composition for inhibiting proteases of the elastase type or for protecting elastic fiber comprising an effective amount of a lipopeptide as defined in claim 1 in admixture with an excipient.

11. A pharmaceutical composition for use in the treatment of arteriosclerosis, pulmonary emphysema, arthrose, diabetes and certain tumors in which elastases are implicated comprising 0.1 to 5 weight percent of a lipopeptide as defined in claim 1 and a pharmaceutically acceptable excipient.

12. A cosmetic composition for the treatment of the skin comprising 0.1 to 2 weight percent of a lipopeptide as defined in claim 1 and a skin compatible excipient.

* * * * *